(12) United States Patent
Corson et al.

(10) Patent No.: US 6,791,690 B2
(45) Date of Patent: Sep. 14, 2004

(54) READING DRY CHEMICAL ARRAYS (75) Inventors: John F. Corson, Mountain View, CA (US); Andreas N. Dorsel, Menlo Park, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 178 days.

(21) Appl. No.: 10/137,658

(22) Filed: Apr. 30, 2002

(65) Prior Publication Data

US 2003/0203371 A1 Oct. 30, 2003

(51) Int. Cl.[7] .................................................. G01N 21/55
(52) U.S. Cl. .................... 356/445; 422/82.08; 435/808
(58) Field of Search ................................. 356/317, 318, 356/417, 436, 440, 445; 250/458.1, 459.1, 461.1, 461.2; 436/164, 166; 422/82.08–82.09, 82.05

(56) References Cited

U.S. PATENT DOCUMENTS

| | | |
|---|---|---|
| 3,542,481 A | 11/1970 | Slomba |
| 3,704,951 A | 12/1972 | Chupp |
| 3,849,654 A | 11/1974 | Malvin |
| 4,052,621 A | 10/1977 | Haas |
| 4,088,407 A | 5/1978 | Schoeffel et al. |
| 4,188,542 A | 2/1980 | Hogg et al. |
| 4,188,543 A | 2/1980 | Brunsting et al. |
| 4,189,236 A | 2/1980 | Hogg et al. |
| 4,199,686 A | 4/1980 | Brunsting et al. |
| 4,222,743 A | 9/1980 | Wang |
| 4,281,924 A | 8/1981 | Auer et al. |
| 4,341,993 A | 7/1982 | Brunsting et al. |
| 4,345,837 A | 8/1982 | Kallet |
| 4,348,107 A | 9/1982 | Leif |
| 4,533,246 A | 8/1985 | Braun |
| 4,549,807 A | 10/1985 | Hoffmaster |
| RE32,598 E | 2/1988 | White |
| 4,737,464 A | 4/1988 | McConnell et al. |
| 4,802,768 A | 2/1989 | Gifford et al. |
| 4,844,613 A | 7/1989 | Batchelder et al. |
| 4,847,508 A | 7/1989 | Kokubu |
| 4,867,559 A | 9/1989 | Bach |
| 4,882,288 A | 11/1989 | North et al. |
| 4,907,883 A | 3/1990 | Allmon et al. |
| 4,931,384 A | 6/1990 | Layton et al. |
| 4,943,159 A | 7/1990 | Oetliker et al. |
| 5,006,716 A | 4/1991 | Hall |
| 5,018,866 A | 5/1991 | Osten |
| 5,026,159 A | 6/1991 | Allen et al. |
| 5,047,213 A | 9/1991 | Finlan et al. |
| 5,055,265 A * | 10/1991 | Finlan ..................... 422/82.09 |
| 5,064,619 A | 11/1991 | Finlan |
| 5,118,608 A | 6/1992 | Layton et al. |

(List continued on next page.)

FOREIGN PATENT DOCUMENTS

WO         WO 99/23492         5/1999

OTHER PUBLICATIONS

Website http://www.biodevice.com/SuperStrate.html., "SuperStrate", bioDevice Partners, 2 pp. downloaded Jan. 27, 2000.
Schalkhammer, Thomas, "Metal Nano Clusters as Transducers for Bioaffinity Interactions", Monatschefte fur Chemie, vol. 129, pp. 1067–1092, 1998.
Stratagene catalog, 1989, p, 39.

*Primary Examiner*—Michael P. Stafira
*Assistant Examiner*—Juan D Valentin, II
(74) *Attorney, Agent, or Firm*—Gordon Stewart (57) ABSTRACT Array units and methods are provided which have constructions to reduce or take advantage of Fresnel reflection. The array units may have a subtantially unreflective substrate. In one arrangement a transparent spacer layer is provided while in another an anti-reflective layer is present.

33 Claims, 4 Drawing Sheets

U.S. PATENT DOCUMENTS

| | | |
|---|---|---|
| 5,127,729 A | 7/1992 | Oetliker et al. |
| 5,173,434 A | 12/1992 | Morris et al. |
| 5,210,411 A | 5/1993 | Oshima et al. |
| 5,315,375 A | 5/1994 | Allen |
| 5,319,975 A | 6/1994 | Pederson et al. |
| 5,322,798 A | 6/1994 | Sadowski |
| 5,327,225 A | 7/1994 | Bender et al. |
| 5,374,563 A | 12/1994 | Maule |
| 5,478,755 A | 12/1995 | Attridge et al. |
| 5,484,571 A | 1/1996 | Pentoney, Jr. et al. |
| 5,611,998 A | 3/1997 | Aussenegg et al. |
| 5,631,734 A | 5/1997 | Stern et al. |
| 5,675,443 A | 10/1997 | Dorsel |
| 5,717,216 A | 2/1998 | McCoy et al. |
| 5,721,435 A | 2/1998 | Troll |
| 5,763,870 A | 6/1998 | Sadler et al. |
| 5,945,679 A | 8/1999 | Dorsel et al. |
| 5,981,956 A * | 11/1999 | Stern ..................... 250/458.1 |
| 6,008,892 A | 12/1999 | Kain et al. |
| 6,025,601 A | 2/2000 | Trulson et al. |
| 6,153,384 A * | 11/2000 | Lynch et al. ................ 435/6 |
| 6,177,990 B1 | 1/2001 | Kain et al. |
| 6,180,351 B1 * | 1/2001 | Cattell ........................ 435/6 |
| 6,232,072 B1 | 5/2001 | Fisher |
| 6,238,862 B1 | 5/2001 | McGall et al. |
| 6,329,143 B1 * | 12/2001 | Stryer et al. ................. 435/6 |
| 6,545,264 B1 * | 4/2003 | Stern ......................... 250/234 |
| 6,627,397 B1 * | 9/2003 | Nakamura et al. ......... 422/68.1 |
| 2002/0001845 A1 * | 1/2002 | Klaerner et al. ............. 436/8 |
| 2002/0055125 A1 * | 5/2002 | Charych et al. ............ 435/7.5 |

* cited by examiner

READING DRY CHEMICAL ARRAYS

FIELD OF THE INVENTION

This invention relates to arrays, particularly biopolymer arrays such as DNA or protein arrays, which are useful in diagnostic, screening, gene expression analysis, and other applications.

BACKGROUND OF THE INVENTION

Polynucleotide arrays (such as DNA or RNA arrays) and peptide array, are known and may be used, for example, as diagnostic or screening tools. Such arrays include regions (sometimes referenced as spots or features) of usually different sequence polynucleotides or peptides arranged in a predetermined configuration on a substrate. The array is "addressable" in that different features have different predetermined locations ("addresses") on a substrate carrying the array.

Biopolymer arrays can be fabricated using in situ synthesis methods or deposition of the previously obtained biopolymers. The in situ fabrication methods include those described in U.S. Pat. No. 5,449,754 for synthesizing peptide arrays, and in U.S. Pat. No. 6,180,351 and WO 98/41531 and the references cited therein for polynucleotides. In situ methods also include photolithographic techniques such as described, for example, in WO 91/07087, WO 92/10587, WO 92/10588, and U.S. Pat. No. 5,143,854. The deposition methods basically involve depositing biopolymers at predetermined locations on a substrate which are suitably activated such that the biopolymers can link thereto. Biopolymers of different sequence may be deposited at different feature locations on the substrate to yield the completed array. Procedures known in the art for deposition of biopolymers, particularly DNA such as whole oligomers or cDNA, are described, for example, in U.S. Pat. No. 5,807,522 (touching drop dispensers to a substrate), and in PCT publications WO 95/25116 and WO 98/41531, and elsewhere (use of a pulse jet in the form of a piezoelectric inkjet head).

Further details of large scale fabrication of biopolymer arrays by depositing either previously obtained biopolymers or by the in situ method, are disclosed in U.S. Pat. No. 6,242,266, U.S. Pat. No. 6,232,072, U.S. Pat. No. 6,180,351, and U.S. Pat. No. 6,171,797.

In array fabrication, the quantities of DNA available for the array are usually very small and expensive. Sample quantities available for testing are usually also very small and it is therefore desirable to simultaneously test the same sample against a large number of different probes on an array. These conditions require the manufacture and use of arrays with large numbers of very small, closely spaced features.

The arrays, when exposed to a sample, will exhibit a binding pattern. The array can be read by observing this binding pattern by, for example, labeling all targets such as polynucleotide targets (for example, DNA), in the sample with a suitable label (such as a fluorescent compound), scanning an illuminating beam across the array and accurately detecting the fluorescent signal from the different features of the array. Assuming that the different sequence polynucleotides were correctly deposited in accordance with the predetermined configuration, then the observed binding pattern will be indicative of the presence and/or concentration of one or more polynucleotide components in the sample. Peptide or arrays of other chemical moieties can be used in a similar manner. Conventionally, the illuminating and detecting have been performed on a dry array from a forward direction facing a front surface of the array carrying the array features, so that the illuminating and detected light need not pass through the substrate. In an alternative known arrangement, a transparent substrate forms part of a chamber in a housing with the array on a front substrate surface facing inward to the chamber. After exposure to a liquid containing the sample, the chamber is flushed and again filled with a liquid and the liquid containing chamber positioned in the array reading apparatus. In this situation, aside from the flushing and re-filling of the chamber, care must be taken that liquid does not leak from the chamber while positioned in the reading apparatus. The illuminating and detecting in this case has, of necessity, been performed in a backward direction through the substrate and onto the array while it is immersed in the liquid.

Techniques and apparatus for scanning chemical arrays are described, for example, in U.S. Pat. No. 5,763,870 and U.S. Pat. No. 5,945,679. Apparatus which reads an array by scanning an illuminating beam by the foregoing technique are often referred to as scanners and the technique itself often referred to as scanning. Conventionally, such scanning has been done by illuminating array features on a front surface of the substrate one pixel at a time.

Array scanners typically use a laser beam as a light source, which is scanned over pixels covering the array features. A detector (typically a fluorescence detector) with a very high light sensitivity is normally desirable to achieve maximum signal-to-noise in detecting hybridized molecules, particularly in array scanners used for DNA sequencing or gene expression studies. At present, photomultiplier tubes ("PMTs") are still the detector of choice although charge coupled devices ("CCDs") and avalanche photodiodes ("APDs") can also be used. PMTs and APDs are typically used for temporally sequential scanning of array features, while CCDs permit scanning many features in parallel (for example, one line of features simultaneously, in which case an illuminating line may be used).

When a sample component only weakly binds to an array feature (due to a low concentration of that component in the sample) the resulting fluorescence signal from that feature will be low. To be able to detect such low signal features, it is important to detect the resulting low signal with a high signal to noise ratio. It is also desirable to have a reading method where a liquid filled chamber containing the array is not positioned within the scanner.

SUMMARY OF THE INVENTION

One of the items recognized by the present invention is that when a dry array on a front surface of a substrate is interrogated or read from a forward position, the power density of the interrogating light or light emitted in response to the interrogating light, or both, can be reduced as a result of Fresnel reflection. This may consequently lead to a reduced detected signal from an array feature.

In one aspect then, the present invention provides a method of interrogating an addressable array unit having a substantially unreflective substrate with a front surface, and a dry array on the front surface having a plurality of different chemical features (for example, polynucleotide features of different sequence). In one configuration the method may include directing an interrogating light from a position forward of the front surface onto the chemical features of the dry array. In an additional or alternative configuration the method may include detecting light directed in a forward direction which is emitted from respective features in response to the interrogating light. The substrate may be substantially unreflective by virtue of there being no metallic or semi-metallic (for example, no silicon) coating present, and can also optionally be a transparent substrate.

In a first configuration, the detected light is emitted from locations of the features positioned within an ⅛ wavelength of an antinode resulting from either directly incident interrogating light (that is, directly incident on the emitting locations) and interrogating light reflected by the substrate (to the emitting locations), or from directly detected emitted light and emitted light reflected by the substrate. That is, the majority (or optionally at least 60%, 70%, 80%, 90% or 95%) of detected light is from such features. In a second configuration the substantially unreflective substrate may include a transparent layer extending between the front surface of the substrate and a next layer, and which transparent layer has a thickness t. This transparent layer may function as a spacer layer or anti-reflective layer, as discussed below, and the thickness t may be any of those values used for distance d discussed below. In a third configuration (which may be in conjunction or not with the first or second configurations), the detected light power density for each of multiple features is within 30% (or 25, 20, 15, or 10%) of a maximum attainable under the same conditions with only the distance of the emitting locations from the front surface being varied, or the detected light power density is at least 10% (or 25, 33, or 50%) greater than attained under the same conditions with the anti-reflection layer absent (in which case the features are attached directly to a front surface of a base layer). By "same conditions" in this context includes the same array/substrate and same instrument (and therefore with the same interrogating light illumination and emitted light detection, as well as the same depth of field for the detected emitted light, and with the focal plane adjusted to the same position relative to the front surface of the substrate).

The detected light may be emitted from locations which are spaced from the front surface of the substrate, or from an interface of two layers of the substrate having different refractive indices, by a distance d wherein:

$$n\lambda/8 < d < (n+2)\lambda/8$$

where n is one or any second odd integer thereafter (that is, a member of the series 1, 5, 9, 13, 17 and so on), and λ is the wavelength of the interrogating light or emitted light in the media from which the layer is made. When the distance d is that from the front surface of the substantially unreflective substrate, one way to accomplish this is by providing features which extend from the front surface by the distance d. When the distance d is that from an interface of two layers of different refractive index, this can be accomplished by one of the layers being a transparent layer of thickness t equal to d as defined above, and which extends between the front surface and a next layer. An alternative way is providing such transparent layer with a thickness which together with the distance which the features extend from the front surface of the substrate, totals to distance d as defined above.

The present invention further provides an addressable array unit of a type used in a method of the present invention. Such an array unit may have a substantially unreflective substrate with a front surface, and a dry array on the front surface having a plurality of different chemical features. In such an array unit the features may extend from the front surface by d above, for example, at least 80 nm (or 100, 125 or 150 nm) to less than 250 nm (or 225, 200, or 17 nm). In another construction, the substrate may include an anti-reflection or spacer layer extending between front surface and a next layer which may have a thickness equal to or less than any of the foregoing thickness ranges. Since the array may not have been exposed to a sample at this point (for example, to a sample containing many fluorescently labeled polynucleotides of different sequence which hybridize to respective polynucleotide array features), this thickness may only provide an indication of the distance by which the light emitting features will be spaced from the front surface of the substrate during reading of the dry array. After exposure to a sample (such as a sample containing fluorescently labeled polynucleotides) the locations from which light is emitted (for example, the fluorescent labels) upon reading of the array may be spaced a distance d as defined above from the substrate front surface. The array unit may optionally include instructions to interrogate the array by a method of the present invention, and/or with one or more parameters described herein (for example, direct the interrogating light onto the front side of the substrate). An identifier carried on the array substrate, or a housing carrying the substrate, may provide such instructions.

In a method of the present invention, the interrogating light may be directed toward the front surface at an angle of less than 50 degrees to a normal to the back surface (such as less than 36, 25, 20. 15, or less than 5 degrees), and more than 0, 1, 2 or 4 degrees, as well as 0 degrees itself (where the interrogating light is perpendicular to the front surface). The same ranges may be used for the detected light leaving the back surface.

The present invention further provides a method for use with an addressable array unit having a transparent substrate with a front surface, and an array with a plurality of different chemical features on a front surface. The method includes reading (such as machine reading) an identifier associated with the array unit (such as by being present on the substrate carrying the array, a housing carrying the substrate, or in or on a same package with the array substrate). An instruction that the array should be interrogated and read from a forward direction (that is, forward of the front surface), is retrieved (such as by a processor) based on the read identifier. The instruction may be retrieved from the read identifier itself, or from a memory using data from the read identifier (for example, the whole or part of the retrieved identifier). The retrieved instruction may be used to check that the array is properly oriented within an array reader such that the array can be interrogated and read by the reader from the forward direction.

Another aspect of the present invention provides an apparatus for reading an array which illuminates the array and detects light emitted in response thereto, from the forward direction in a manner as already described. The apparatus includes a light source to provide the interrogating light, and a detector to receive the emitted light. A processor receives the data from the detector and may save the results (either further processed or raw) in a memory. The processor may also execute any other method of the present invention, such as retrieving the instruction based on the read identifier, and checking that the array is properly oriented such as based on signals received from the detector or another means (for example, based on whether an indicia, such as the identifier or other indicia, is facing in the correct direction corresponding to proper orientation of the array in the apparatus). The present invention further provides a computer program product for use with such a chemical array reader apparatus. The computer program product comprises a computer readable storage medium having a computer program stored thereon which, when loaded into the processor, causes the reader to execute a method as describe herein.

While the methods and apparatus have been described in connection with arrays of various moieties, such as polynucleotides (for example, DNA), it will be understood throughout this description that other moieties can be used and may include any chemical moieties such as other biopolymers or polymers.

The present invention can provide any one or more of the following or other benefits. For example, one or more advantages of reading an array from the front side (for example, relative insensitivity to typical substrate defects or thickness, back surface quality, and variations in refractive index) may be obtained while reducing deleterious signal loss due to Fresnel reflections.

BRIEF DESCRIPTION OF THE DRAWINGS

Embodiments of the invention will now be described with reference to the drawings, in which.

To facilitate understanding, the same reference numerals have been used, where practical, to designate similar elements that are common to the FIGS.

DETAILED DESCRIPTION OF THE INVENTION

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

An "array", unless a contrary intention appears, includes any one-, two- or three-dimensional arrangement of addressable regions bearing a particular chemical moiety or moieties (for example, biopolymers such as polynucleotide sequences) associated with those regions. An array is "addressable" in that it has multiple regions of different moieties (for example, different polynucleotide sequences) such that a region (also referenced as a "feature" or "spot" of the array) at a particular predetermined location (an "address") on the array will detect a particular target or class of targets (although a feature may incidentally detect non-targets of that feature). Note that the finite small areas on the array which can be illuminated and from which any resulting emitted light can be simultaneously (or shortly thereafter) detected, define pixels which are typically substantially smaller than a feature (typically having an area about $\frac{1}{10}$ to $\frac{1}{100}$ the area of a feature). Array features are typically, but need not be, separated by intervening spaces. In the case of an array, the "target" will be referenced as a moiety in a mobile phase (typically fluid), to be detected by probes ("target probes") which are bound to the substrate at the various features. However, either of the "target" or "target probes" may be the one which is to be evaluated by the other (thus, either one could be an unknown mixture of polynucleotides to be evaluated by binding with the other). An "array layout" refers to one or more characteristics of the features, such as feature positioning on the substrate, one or more feature dimensions, and an indication of a moiety at a given location. The array "substrate" includes everything of the array unit behind the substrate front surface. "Hybridizing" and "binding", with respect to polynucleotides, are used interchangeably.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top", "upper", and "lower" are used in a relative sense only. Wavelengths are peak wavelengths unless otherwise indicated. By "transparent" is referenced a substrate which transmits, within the substance, at least 80% (or even at least 85%, 90%, 95%, or 98%) of both the interrogating and emitted light as measured at the peak wavelengths. These transmission figures represent transmission within the substance and exclude any account of Fresnel reflection that may occur upon light entering the substance at an interface of that substance and another medium (for example, the interface of a surface of the substance and the ambient atmosphere). By "reflective" material is a material which reflects at least 60% (or even at least 80% or 90%) of light of the interrogating or emitted wavelength as a result of the nature or construction of the material and not as a result of Fresnel reflection. Such reflective materials may include a metal or semiconductor (for example, silicon) layer.

By "substantially unreflective substrate", is referenced a substrate which reflects less than 10% of the power density of light at 530 nm or 630 nm directed onto the front surface of the substrate at an angle of ninety degrees thereto. However, a substrate could be used which is less reflective than this, for example reflecting less than 8%, 6%, 5%, or even less than 4% or 2% of the foregoing light power density.

Wavelengths are measured in a gas (such as air or nitrogen), or a vacuum, whichever one is in contact with the dry array during reading, unless the contrary is indicated. For example, for many illuminating light peak emissions (such as about 530 nm or 630 nm) and different emitted light peak emissions (such as 550 nm to 610 nm, or 650 nm to 730 nm), the light may be emitted from locations which are less than 50 nm, less than 20 nm, or even less than 10 nm from the front surface of the substrate.

A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station. Reference to a singular item, includes the possibility that there are plural of the same items present. "May" means optionally. Methods recited herein may be carried out in any order of the recited events which is logically possible, as well as the recited order of events. All patents and other references cited in this application, are incorporated into this application by reference except insofar as they may conflict with those of the present application (in which case the present application prevails).

Figure 1:
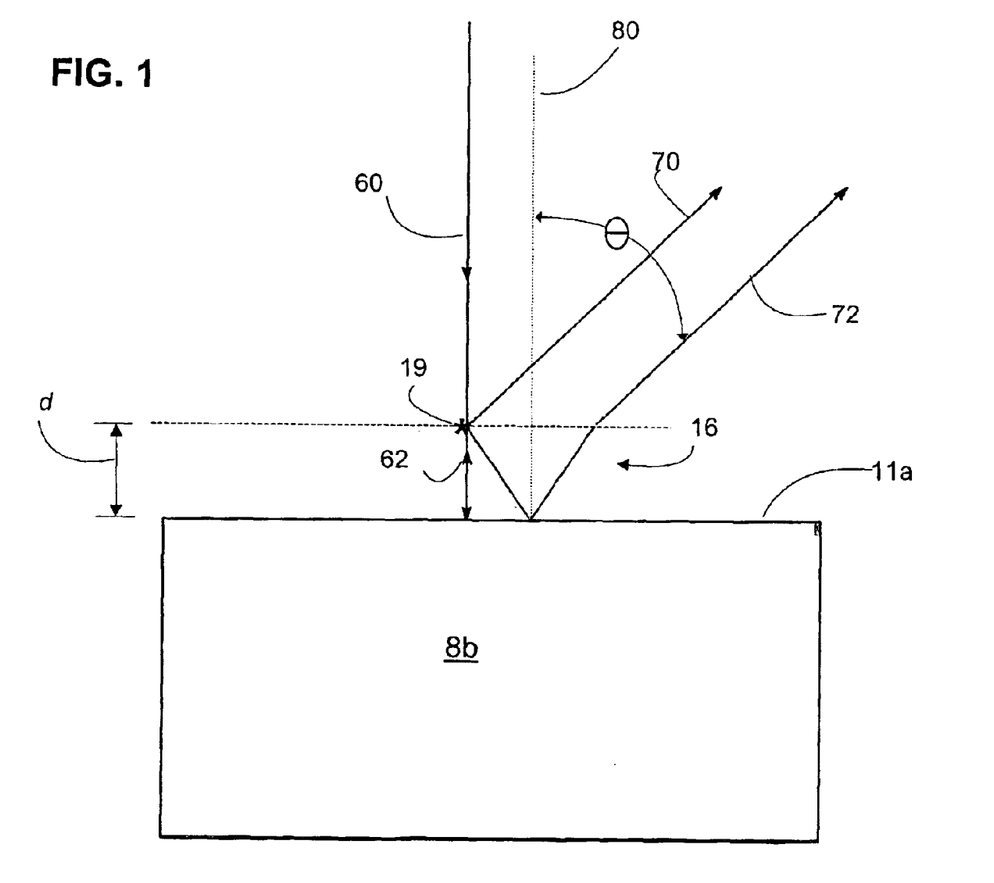
FIG. 1 illustrates Fresnel reflection considerations in the reading of an array.

The present invention recognizes that Fresnel reflection can cause undesirable loss of detected signal from array features, but that the array can be constructed to take advantage of Fresnel reflection. This can be understood with reference to FIG. 1. In FIG. 1 an interrogating beam of light 60 may be incident at (or close to) a normal 80 to a surface 11a on a base layer 8b. A fluorescent label 19 to be detected will then be exposed to directly incident light 60 (that is, light which is directly incident on label 19). However, as a result of Fresnel reflection a portion of light 60 will be reflected at front surface 11a as light 62. The relative amplitude, $A_r$ of the reflected light 62 in relation to the incident light 60 is given by the equation:

$$A_r = (1-p)/(1+p) \tag{1}$$

where $p=n1/n3$ in which n1 is the refractive index of the medium adjacent front surface 11a (usually air) while n3 is the refractive index of base layer 8b. Assuming the substrate is read in air and assuming a base layer 8b of glass with an n3 of approximately 1.5, this leads to an $A_r$ of about 20%. The amplitude of the electric-field of the reflected light is the square root of the power density, or in the foregoing case the square root of 0.04 (intensity of reflection) which gives 0.2 times the amplitude of the power density of incident light 60. Furthermore, because the reflection occurs at an interface going from a lower index of refraction n1 to a higher index of refraction n3, the phase of the reflected field of light 62 is exactly 180 degrees out of phase with that of the light 60. Thus, immediately at front surface 11a in this situation, the reflected electric field will partially cancel that of the incident field. Thus, the power density of the incident light 60 at surface 11a is, reduced to 0.64 times the original power density (0.8 squared). More generally, assuming an incident light 60 angle which is normal to surface 11a, the illumination power density, PF, at feature 19 is given by:

$$P_F = P_0(1-\sqrt{R})^2 \tag{2}$$

where R is the Fresnel reflection and $P_0$ is the incident light power. At more oblique incidence the portion of the incident electric field polarized not parallel to the surface will not be fully parallel with the reflected field and therefore will not show the full effect.

Usually in an array the fluorescent label 19 lies close to surface 11a (about 20 nm or 10 nm, or less). At that distance from surface 11a the label 19 will see the electric field diminished by nearly the full amount (down to 0.64) of the incident light. This will be true provided that the wavelength of the interrogating light is large compared to twice the distance, d, from the surface 11a to label 19. In addition though, light emitted from labels 19 in such a location, in response to the interrogating light will suffer similar degradation of power density due to interference. In particular, light emitted from label 19 can be thought of as a combination of light emitted directly away from label 19 in a forward direction and light emitted toward surface 11a. The light emitted toward surface 11a will be partially reflected at surface 11a as a result of Fresnel reflection, in a similar manner as light 60. Thus, the actual light emitted from label 19 in the forward direction away from surface 11a will be reduced in power density to 64% of that which would be obtained absent the Fresnel reflection. The combination of destructive interference resulting from Fresnel reflection of the interrogating light and Fresnel reflection of the emitted light, can therefore reduce the total emitted light power density down to approximately 41% (0.64×0.64) of the power density which would be obtained absent any Fresnel reflection. More generally the emitted light detected at an angle normal to surface 11a is given by:

$$F_F = F_0(1-R)^2 \tag{3}$$

where $F_0$ is the initial fluorescence from label 19 absent any Fresnel reflection. However, again this is only exactly true for normal incidence of light 60.

The present invention proposes several ways in which one or both of these power density losses resulting from Fresnel reflection can be reduced. One technique to reduce this loss is to use a very oblique angle of incidence for the interrogating light and for detection of emitted light. Another technique in which power density loss from Fresnel reflection could be reduced, is to position label 19 at a distance, d, above front surface 11a or an interface of layers in the substrate having different indices of refraction. For example, d may be about 0.25λ. One way of obtaining this distance, when measured from a layer interface, is by the use of an anti-reflection coating or layer to reduce Fresnel reflection. Anti-reflection coatings are known in other optics technologies and are described in detail in, for example,—Hecht—Optics $2^{nd}$ ed. Page 375. Such anti-reflection coatings may have a thickness t which is equal or close to distance d defined above, such as about 0.25λ in thickness, or some odd integral multiple of this thickness (although thinner layers tend to result in less mechanical stress), where A is the wavelength of the interrogating or emitted light in the media from which the layer is made (or, where these two wavelengths are different a wavelength intermediate the two, for example mid-way, may be selected as a good compromise). Known coating materials and methods are available which can reduce the reflection to 0.5% power density from a normal incidence of light onto a glass surface. This would mean a reflected electric field amplitude of only 0.07. In this case, the total field amplitude after interference would be 0.93 (0.93=1.00−0.07). The total power density after interference would be 0.86 times the incident power density. If this number is squared, for the reduction in incident light as well as emitted fluorescent light, the total emitted power density from a label 19 is 75% of the power density which would be obtained in the absence of the anti-reflection layer and any Fresnel reflection. This is a factor of 1.82 (0.75/ 0.41) better than without the anti-reflective layer.

Another way in which this distance d can be obtained, when measured from a layer interface, is to provide a spacer layer (which spacer layer has an index of refraction n2 as close to 1 as practical and which has a thickness, t, which is equal to distance d as defined herein, such as approximately 0.25λ.

Figure 4:
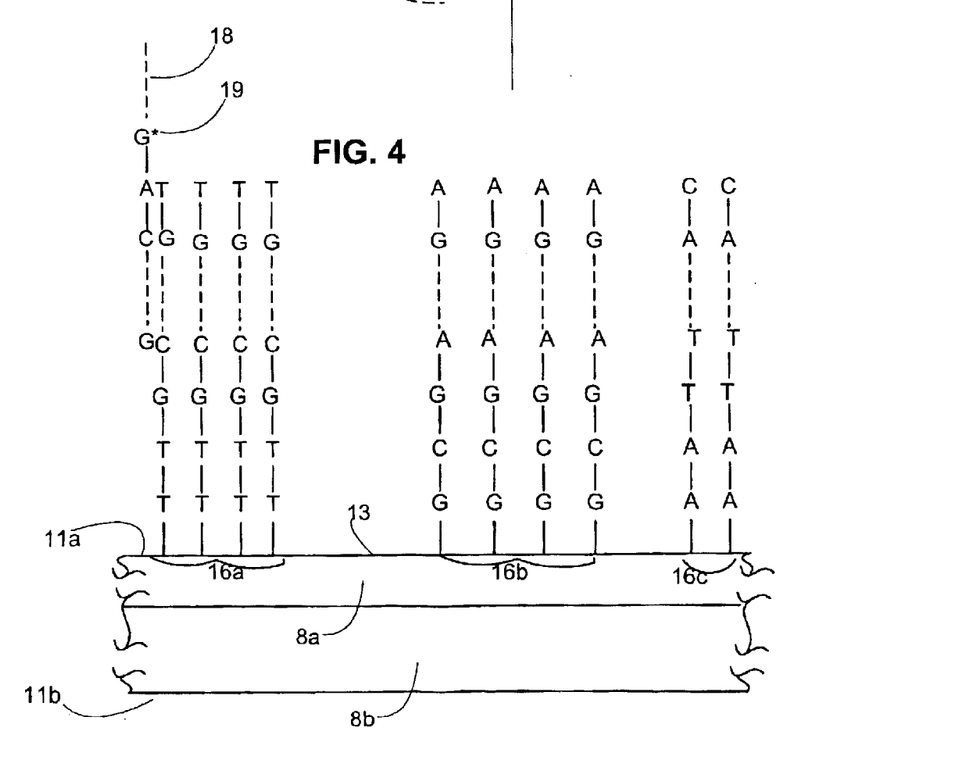
FIG. 4 is an enlarged cross-section of a portion of FIG. 3.

A layer 8a which may serve as a spacer or anti-reflective layer, is illustrated in FIG. 4. If such a layer is present with a thickness t equal to d, then the locations from which the detected light is emitted should be as close as possible to the front surface of the substrate (for example, less than 20 nm or less than 10 nm from the front surface).

A further way in which the above distance d can be obtained, when measured from the front surface 11a, is by using a long chain linker molecule (a "stilt") to ensure separation of label 19 from surface 11a by the same amount. However, a combination of spacer layer and stilt could be used which together position label 19 by distance, d, above the foregoing layer interface.

Providing such a spacer layer or stilts have a low index of refraction (ideally, as close to possible to that of the atmosphere at surface 11a) the Fresnel reflection at the surface 11a will still yield nearly 4% of incident light power density. However, with the foregoing spacer layer and/or stilts the reflected field will be nearly in phase with the light directly incident on label 19. This is because the 180 degree phase shift which occurs at surface 11a (since the light is traveling from a lower index of refraction, n1, to a higher index, n3) is added to two 90 degree phase shifts due to the approximately quarter wavelength of distance traveled both to and from surface 11a, resulting in 360 degrees total phase shift. That is, assuming the wavelength of the interrogating and emitted light are close to one another, label 19 will be positioned close to an antinode resulting from constructive interference of directly incident interrogating light and interrogating light reflected from the front surface of the transparent substrate, as well as an antinode resulting from constructive interference of directly emitted light (that is, light emitted in a forward direction without any reflection) and emitted light reflected from the front surface 11a. In this case, for the interrogating light alone the total electric field at label 19 after interference would be 1.2 times the electric field from directly incident interrogating light alone, and the light power density 1.44 times the light power density obtained absent the spacer layer or stilts. This number is squared since a same result is obtained for emitted light from label 19 by itself, resulting in a total emitted light power density 2.07 times greater than would be obtained absent a spacer layer and/or stilts as described. In total then, the total emitted light power density can be increased by a factor of 5.05 times (2.07/0.41) that obtained absent the spacer layer or stilts as described.

Suitable stilts are linked to the front surface of the substrate and may include non-nucleotide polymers with a backbone comprising carbon atoms, which are linked to the front surface of the substrate. Polynucleotide stilts may also be used which are at least 10 nucleotides and homopolymeric or contains only three of the four possible nucleotides. Inorganic long-chain polymers may also be used as stilts in which, for example, less than 40%, 20%, 10% or 5% of the backbone atoms are cross-linked.

It will be appreciated though, that the above description is for interrogating light being incident on surface 11a from a position normal thereto, and with the emitted light being detected from a forward position which is also normal to surface 11a. If the angle θ of incidence between the interrogating light or the detection angle and the normal to surface 11a, is increased, the gains in emitted light power density discussed above will be decreased in a known manner as is well understood in connection with Fresnel reflection. In particular if incident radiation on surface 11a is considered as the superposition of two plane-polarized beams, one with its electric field parallel to the plane of incidence (p-polarized) and the other with its electric field perpendicular to the plane of incidence (s-polarized), Fresnel's laws can be summarized by the equations:

$$r_s = \left[\frac{\sin(\theta_1 - \theta_2)}{\sin(\theta_1 + \theta_2)}\right]^2 \tag{4}$$

$$r_p = \left[\frac{\tan(\theta_1 - \theta_2)}{\tan(\theta_1 + \theta_2)}\right]^2. \tag{5}$$

$r_S$ and $r_p$ are the reflectance of the s- and p-polarized components in terms of proportion of the original electric field strengths, and where θ1 is the incident light angle and θ2 is the refracted light angle, both as measured in relation to the normal 80 to surface 11a. These reduce to equation (1) for incident light normal to an interface.

Furthermore, an ideal value of the distance, d, which is measured in this application as normal to the surface 11a, may also vary somewhat for interrogating light 60 incident at an angle θ to normal 80, since the light is traveling further through the anti-reflection or spacer layer. The same consideration applies for the angle θ at which the emitted light is detected. This is illustrated in FIG. 1 for an emitted light from label 19 detected along path 70 with a corresponding reflected light along path 72. However, in constructing an array for various uses, reasonably good results for interrogating and emitted light power density can be obtained where the distance d is based on an angle of interrogating light and angle of detection of emitted light both assumed to be normal to surface 11a, provided that during reading of the array the actual values of these angles are kept relatively small (for example, if not 0 degrees then less than 25 degrees, or less than 15, 10, 5 or 2 degrees).

Figures 2, 3:
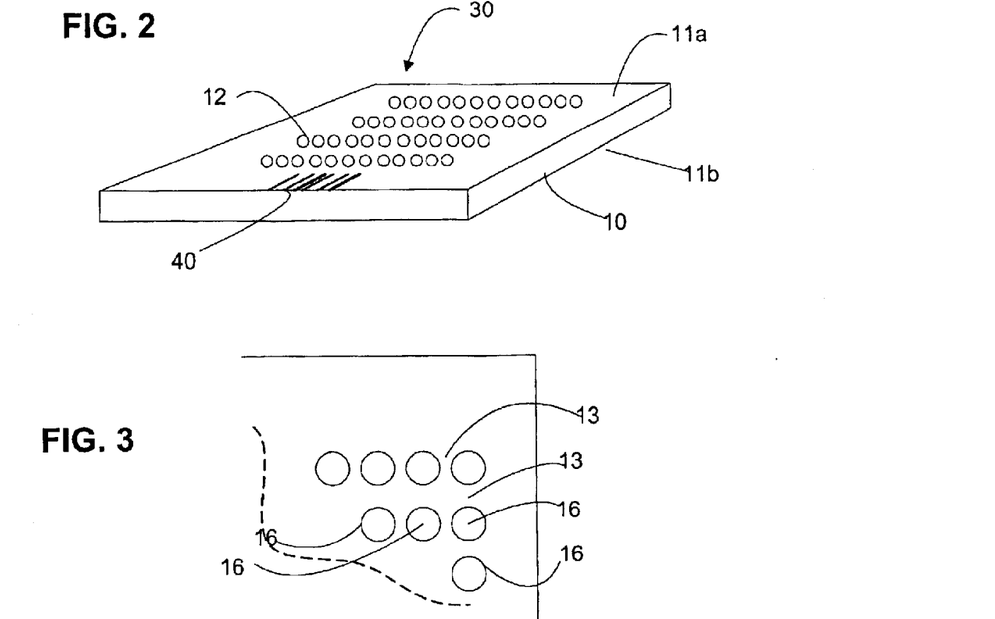
FIG. 2 is a perspective view of an array unit of the present invention.
FIG. 3 is an enlarged view of a portion of FIG. 2 showing some of the identifiable individual features of a single array of FIG. 2.

Referring now to FIGS. 2–4, an array unit 30 of the present invention includes a contiguous planar transparent substrate 10 carrying multiple features 16 disposed across a front surface 11a of substrate 10 and separated by interfeature areas 13. Features 16 are disposed in a pattern which defines the array. A second surface 11b of substrate 10 does not carry any features. Substrate 10 may be of any shape although the remainder of any unit carrying substrate 10, and the apparatus of the present invention, may need to be adapted accordingly. Substrate 10 is substantially unreflective, as defined above. A typical array may contain at least ten features 16, or at least 100 features, at least 1,000, at least 100,000 features, or more. All of the features 16 may be of different composition, or some could be the same (for example, when any repeats of each feature composition are excluded the remaining features may account for at least 5%, 10%, 20%, or 50% of the total number of features). Each features carries probes in the form of a one moiety or mixture of moieties, which in the case of each feature 16 in FIGS. 2–4 is a polynucleotide having a particular sequence, while interfeature areas 13 do not carry any moieties of a type the same as the features 16 (for example, no polynucleotides in the case of features 16 carrying polynucleotides). This is illustrated schematically in FIG. 4 where regions 16 are shown as carrying different polynucleotide sequences. Features 16 may have widths (that is, diameter, for a round spot) of at least 5 or 10 μm, and less than 1.0 cm. In embodiments where very small spot sizes or feature sizes are desired, each of the features 16 may have widths of at least 1.0 μm and less than 1.0 mm, usually less than 500 μm, and more usually less than 200 μm. Features which are not round may have areas equivalent to the area ranges of round features 16 resulting from the foregoing diameter ranges. The probes of features 16 are typically linked to substrate 10 through a suitable linker, not shown.

Substrate 10 may optionally include a transparent spacer or anti-reflective layer 8a extending between front surface 11a to a next layer in the form of base layer 11b. As will be apparent from the discussion herein, if layer 8a is a spacer layer it should be formed of a material which has as low a refractive index as possible (for example, less than 1.3, 1.25, 1.2 or 1.15, or even less than 1.1) while being between the index of refraction of the ambient atmosphere (approximately 1) and that of base layer 8b. For glass substrates, suitable materials for a spacer layer 8a may include an aerogel or sol-Gel (H Floch and P. Belleville in "Sol-Gel Optics IV", B. S. Dunn, J. D. Mackenzie, E. J. Pope, H. K. Schmidt, M. Yamane eds., Proc. SPIE vol 3136 (1997) 275–283), as well as a PPXC/SiO2 layer described by Senkevich, Jay J. "J. Vac. Sci. Tech. B, vol 18, no 1, (2000) page 321).

If, on the other hand, layer 8a is an anti-reflective layer it should ideally have an index of refraction approximately mid-way between that of base layer 8b and the ambient atmosphere above front surface 11a (referenced as n1, which will typically be the refractive index of air of about 1). For example, an anti-reflection layer 8a may have an index of refraction, n2, of at least 1.2 or 1.3. Regardless of whether layer 8a is a spacer layer or anti-reflective layer, base layer 8b may have a refractive index, n3, greater than that of an anti-reflection layer 8a, such as an index of at least 1.3, or 1.4 (or 1.45 or 1.5). However, if layer 8a is to serve as an anti-reflective layer, then the refractive index ratio across the interface of the ambient atmosphere to layer 8a (n2/n1) should be close to equal the refractive index ratio across the interface at layer 8a and base layer 8b (n3/n2). That is, ideally n2/n1=n3/n2. For example, if the refractive index of air is taken as 1 and base layer 8b is glass with a refractive index of 1.5, then ideally layer 8a should have a refractive index of 1.22 so that the refractive index ratios are 1.22=1.5/1.22. When layer 8a is an anti-reflective layer the difference in these refractive index ratios, that is, n3/n2 minus n2/n1 may be less than 0.3, 0.25, 0.2 or less than 0.1. When layer 8a is a spacer layer, the value of n3/n2 minus n2/n1 may be greater than 0.25, 03. 0.4 or 0.5. Suitable materials for an anti-reflective layer with a base layer of glass include, for example, MgF2 and silica. Suitable materials for base layer 8b include, for example, silica, glass, sapphire, or a plastic (that is, a synthetic or processed high molecular weight polymer that is, or is not, thermosetting or thermoplastic). Base layer 8b may have a thickness of at least 1 micrometer (or at least 5, 10 or 100 micrometers, or at least 1 mm).

Layer 8a, whether an anti-reflective or spacer layer, will typically have a thickness, t, equal to or less than a distance d given by the formula:

$$n\lambda/8 < d < (n+2)\lambda/8 \qquad (6)$$

where n is one or any second odd integer thereafter (that is, a member of the series 1, 5, 9, 13, 17 and so on), and λ is the wavelength of the interrogating light or emitted light in the media of the surface layer. For example, d could be greater than 0.15, 0.20, or 0.23 times λ, and less than 0.375 (such as less than 0.35, 0.30, or 0.27) times λ. Typical values of in air are about 530 nm or 630 nm for the interrogating light and such as 550 nm to 610 nm, or 650 nm to 730 nm for the emitted light. As discussed above, these values are peak values. So various values for d are, for example, from any of 80 nm, 100 nm, or 125 nm, to any of 175 nm, 200 nm, or 250 nm.

Both layer 8a, when present, and base layer 8b may be transparent to the wavelength of the interrogating and detected emitted light. The front surface 11a of substrate 10 may be modified with one or more different layers of compounds that serve to modify the properties of the surface in a desirable manner. Front surface 11a should ideally exhibit a low level of binding during hybridization or other events. Substrate 10 may be constructed so as not to have any layer of reflective material in or on it.

The array 12 may cover an area of less than 100 cm$^2$, or even less than 50, 10 or 1 cm$^2$. In many embodiments, substrate 10 will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm.

An array identifier 40 in the form of a machine readable bar code in FIG. 2, is associated with the array 12, by being provided on the same substrate 10 adjacent one of the arrays 12. Of course, codes other than a bar code could be used (for example, a solid state or magnetic memory carrying the identifier 40 could be provided). In the case where more than one array 12 is present on the same substrate 10, a separate identifier can be provided adjacent each corresponding array 12 if desired. Identifier 40 may either contain information on the layout of array 12 as well as any one or more of the following instructions or information or be linkable to a file containing one or more of the following instructions or information in a manner such as described in U.S. Pat. No. 6,180,351: that an interrogating light should be directed from a direction forward of the front surface (that is, above front surface 11a as viewed in FIG. 4); that the emitted light should be detected from forward of the front surface; that the array should be dry when read; the wavelength and angles of the interrogating light; and the wavelength and angles of the detected emitted light; information on the thickness of a spacer or anti-reflection layer 8a. Each identifier 40 for different arrays may be unique so that a given identifier will likely only correspond to one array 12 or to arrays 12 on the same substrate 10. This can be accomplished by making identifier 40 sufficiently long and incrementing or otherwise varying it for different arrays 12 or arrays 12 on the same substrate 10, or even by selecting it to be globally unique in a manner in which globally unique identifiers are selected as described in U.S. Pat. No. 6,180,351.

Arrays such as those of FIGS. 2–4 can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, other array fabrication method may be used such as described in U.S. Pat. No. 5,599,695, U.S. Pat. No. 5,753,788, and U.S. Pat. No. 6,329,143. Interfeature areas 13 need not be present particularly when the arrays are made by light directed methods as described in those patents.

In use, the features 16 of array 12 are simultaneously exposed to a sample such as by contacting the different features 16 simultaneously with a layer of the same sample fluid, such that at least some of the features bind to respective moieties in the sample which sample moieties include the fluorescent label. For example, different polynucleotide sequences at respective features 16 can each hybridize to a complementary sequence, such as polynucleotides at feature 16a in FIG. 4 hybridizing to, and detecting, polynucleotide 18 from the sample. The "*" on polynucleotide 18 indicates a label 19, such as a fluorescent label, of a detected polynucleotide 18. Such labels 19 are the molecular sub-groups which act as locations which emit light in response to the interrogating light. In the case where an anti-reflective or spacer layer 8a is present, labels 19 may be spaced from front surface 11a by a distance less than one-twentieth, or less than one-fortieth or one-fiftieth the wavelength of the interrogating light beam. For example, this distance which may be referenced as a feature "thickness" 20 (see FIG. 6) of the probes at features 16 (which includes any detected target 18 to which probes are bound), is often less than 20 nm, or even less than 10 nm from the front surface 11a of the substrate. In the case where the array has not yet been exposed to a sample, the feature thickness 20 may have any of the foregoing values although it will not include any target 18 (nor any labels in this situation where the target is labeled). Ideally, where layer 8a is a spacer layer then the total value of thickness 20 plus the thickness of such spacer layer 8a is any of those values for distance d discussed above. Alternatively, if there is no anti-reflective or spacer layer 8a feature thickness 20 can be any of those values of the distance d described above. In either case, this will position labels 19 close to a distance of $0.25\lambda$ from front surface 11a, such that during use of the array labels 19 will be at or close to an antinode resulting from either directly incident interrogating light and interrogating light reflected from front surface 11a due to Fresnel reflection, or from directly detected emitted light and emitted light reflected from the front surface 11a due to Fresnel reflection (and ideally at an antinode of both). If layer 8a is an anti-reflective layer then destructive interference of light from Fresnel reflection at front surface 11a and Fresnel reflection at the interface of layers 8a and 8b, will prevent or reduce the power density of any reflected light from front surface 11a in a manner typical of the operation of an anti-reflective layer. Such a reduction in the power density of any reflected light in the foregoing manner reduces possible interference with light coming from a forward direction toward front surface 11a (whether this light is the interrogating light or light emitted from labels 19 in response to the interrogating light) and thereby enhances the power density of illuminating light at labels 19 or the power density of the detected light, as discussed above in connection with FIG. 1.

Thickness 20 can be controlled by selecting polynucleotide or other probes, and their labeled targets (when present), at features 16 which, even if maximally extended in a straight line perpendicular to the surface, would not have a length greater than the foregoing. For example, for naturally occurring polynucleotides the spacing between adjacent base pairs is about 0.35 nm. Thus, even features single-stranded probes of 60 bases in length would only be about 21 nm in thickness (not including bound target length which may extend from the end of the probes). In practice, the actual thickness is far less than the straight line length this since polynucleotide probes will not stand vertical to front surface 10a nor will they be straight. For example, in practice single-stranded probes of 60 nucleotides in length which are bound by their ends to front surface 11a will form a feature of less than 10 nm in thickness. However, in the case where it is desired to have labels 19 positioned at a distance d from front surface 11a without an anti-reflection or spacer layer (or with a spacer layer and thickness 20 which together have a total thickness of d), very long linkers can be used to link the probes to the surface. One way of forming such long linkers is by polymerization beginning from an initiator bound to the front surface 11a, such as described in U.S. patent application Ser. No. 10/005,577 filed Dec. 3, 2001 by Lefkowitz et al. and titled "Surface With Tethered Polymeric Species For Binding Biomolecules".

Note that all thickness values as described herein are measured when the array is dry. Atomic force microscopy may particularly be used for feature thickness, with grazing x-ray reflectivity being particularly useful for measuring the thickness of a film in the range of 10 to 10,000 Angstroms. The thickness of layer 8a though may be measured using laser interferometry or ellipsometry. Additionally, another way to evaluate whether the light emitting locations are spaced an appropriate distance from front surface 11a, or whether layer 8a (whether a spacer or anti-reflection layer) when present is an appropriate thickness, is to prepare multiple arrays with only the distance of the emitting locations from the front surface being varied or layer thickness 8a (when present) being varied, but which arrays are otherwise the same. Each of these prepared arrays may then be interrogated under the same conditions with laser light of wavelength $\lambda$ and the power density of the detected emitted light in response thereto measured for the different arrays but otherwise under the same conditions. Detected emitted light power density from a feature or pixel can then be plotted for the different arrays feature for the different distances or thickness. When sufficient arrays with different distances d or layer 8a thickness are used, a curve with minimum and maximum values will be seen. A suitable correct distance or layer thickness 8a can be taken as one which yields a detected emitted light power density which is within 30% (or 25, 20, 15, or 10%) of the maximum value of this curve.

Alternatively, in the case of an anti-reflection layer 8a the detected emitted light power density can be compared against that for an array which is otherwise the same (in which case the features are attached directly to a front surface of a base layer) and which is interrogated under the same conditions. In this case, a suitable anti-reflection layer 8a thickness is taken as one which yields a detected emitted light power density of at least 10% (or 25, 33, or 50%) greater than attained under the same conditions but with the anti-reflection layer absent. As another alternative, the anti-reflective layer can be such as to reduce the light power density of reflected light to at least 50% (or at least 30%, 20%, or 10%) of that which would be reflected from the substrate under the same conditions but with the anti-reflective layer absent.

Figure 5:
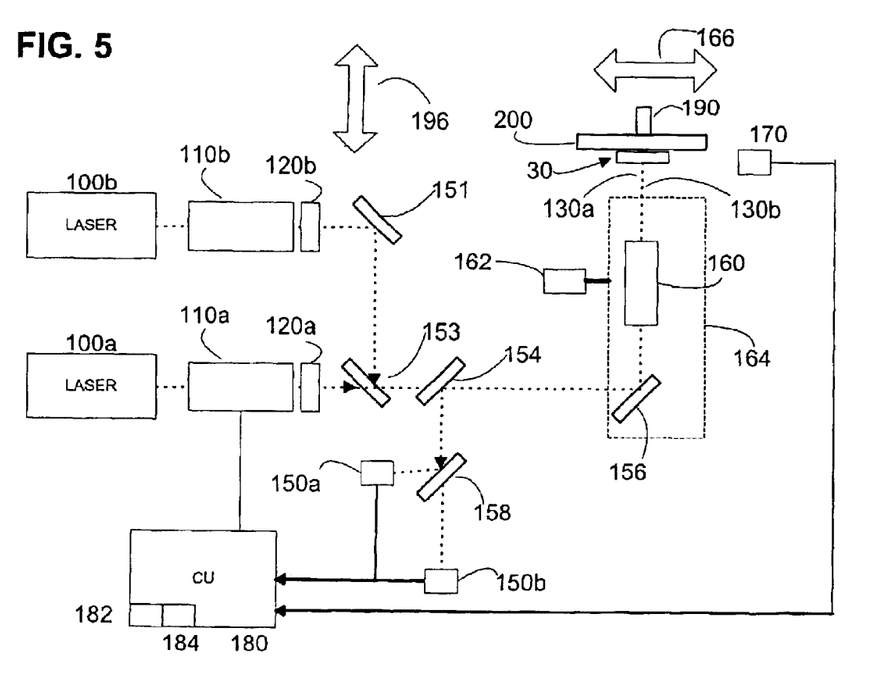
FIG. 5 schematically illustrates an apparatus of the present invention.
Figure 6:
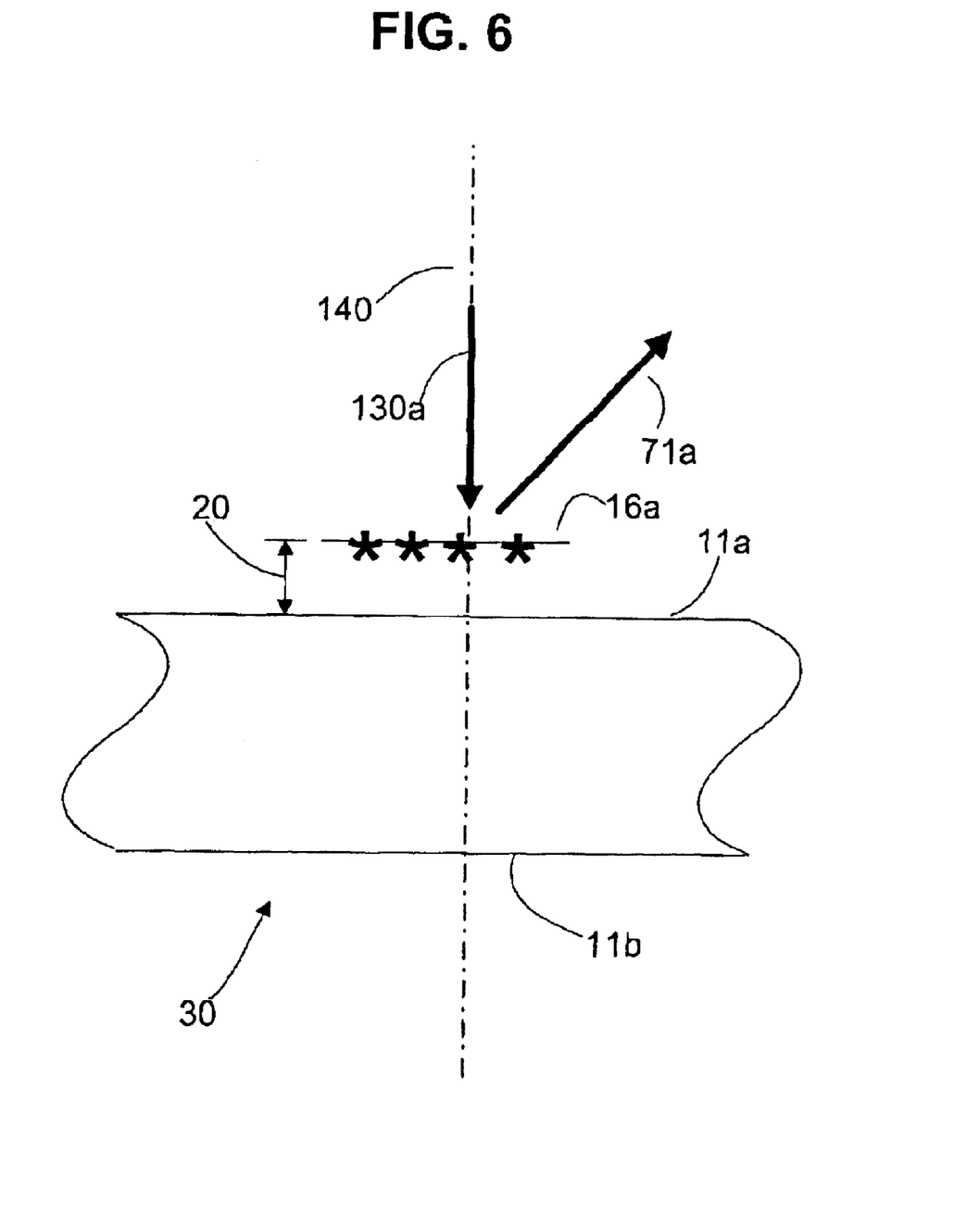
FIG. 6 illustrates components of the apparatus of FIG. 4 in more detail.

Referring now to FIGS. 5 and 6, an apparatus of the present invention (which may be generally referenced as an array "scanner") is illustrated. A light system provides coherent light from a laser 100 which passes through an electro-optic modulator (EOM) 110 with attached polarizer 120. Each laser 100a, 100b may be of different wavelength (for example, one providing red light and the other green) and each has its own corresponding EOM 110a, 110b and polarizer 120a, 120b. The resulting interrogating light beams are coherent and monochromatic, and are directed along respective paths 130a, 130b toward a holder 200 by the use of full mirror 151 and dichroic mirror 153. While FIG. 5 shows these paths as being coincident for the sake of simplicity, the two may in fact be separated by an angle so as to illuminate an array at different locations. This angle of separation may be such that each interrogating light beam is directed along path 130a, 130b toward front surface 11a at an angle equal to or greater than 0 degrees, to 45 degrees to a normal to the back surface (for example less than 1 degree, such as 0.5 degrees). Such an arrangement allows the two interrogating light beams to pass through the same optical system while reducing saturation of fluorescent labels at features 16 as well as channel cross-talk. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power density of an interrogating light spot exiting from the attenuator. The remainder of the light from both lasers 100a, 100b is transmitted through a dichroic beam splitter 154, reflected off fully reflecting mirror 156 and focused onto an array 12 of an array unit 30 mounted on holder 200, using optical components in beam focuser 160. Light emitted, in particular fluorescence, at two different wavelengths (for example, green and red light) from features 16, in response to the interrogating light, is imaged using the same optics in focuser/scanner 160, and is reflected off mirrors 156 and 154. The two different wavelengths are separated by a further dichroic mirror 158 and are passed to respective detectors 150a and 150b. More optical components (not shown) may be used between the dichroic and each detector 150a, 150b (such as lenses, pinholes, filters, fibers etc.) and each detector 150a, 150b may be of various different types (e.g. a photo-multiplier tube (PMT) or a CCD or an avalanche photodiode (APD)). All of the optical components through which light emitted from an array 12 in response to the illuminating laser light, passes to detectors 150a, 150b, together with those detectors, form a detection system. This detection system has a fixed focal plane.

The illumination of features 16 on dry array 12 is more clearly seen in FIG. 6. FIG. 6 illustrates light from laser 100a and resulting emitted light detected on path 71a. However, a similar configuration results from interrogation with light from laser 100b and resulting detected emitted light (although paths 130a and 130b may be slightly spaced apart at array 12 if they are separated by an angle in the manner previously described). Note that, as more clearly seen in FIG. 6, the interrogating light from both lasers is directed from forward of the front surface 11a and onto the chemical features of the dry array 12, while the emitted light is detected from a forward direction. Neither interrogating light on paths 130a, both without passing through substrate 10.

A scan system causes the illuminating area in the form of a light spot from each laser 100a, 100b, and a detecting are of each detector 150a, 150b (which detecting area will form a pixel in the detected image), to be scanned across multiple regions of an array package 30 mounted on holder 200. In this manner, each of the multiple features 16 of the array is read, with each read feature containing multiple pixels (for example, more than five, ten, or twenty). In particular the scanning system is typically a line by line scanner, scanning the interrogating light spot in a line across an array 12 when at the reading position, in a direction of arrow 166, then moving ("transitioning") the interrogating light in a direction into/out of the paper as viewed in FIG. 5 to a position at an end of a next line, and repeating the line scanning and transitioning until the entire array 12 has been scanned. This can be accomplished by providing a housing 164 containing mirror 158 and focuser 160, which housing 164 can be moved along a line of pixels (that is, from left to right or the reverse as viewed in FIG. 5) by a transporter 162. The second direction 192 of scanning (line transitioning) can be provided by second transporter which may include a motor and belt (not shown) to move holder 200 along one or more tracks. The second transporter may use a same or different actuator components to accomplish coarse (a larger number of lines) movement and finer movement (a smaller number of lines). The reader of FIG. 5 may further include a reader (not shown) which reads an identifier 40 from an array package 30. When identifier 40 is in the form of a bar code, that reader may be a suitable bar code reader.

An autofocus detector 170 is also provided to sense any offset between different locations on array 12 when in the reading position, and a determined position of the focal plane of the detection system. An autofocus system includes detector 170, processor 180, and a motorized adjuster to move holder in the direction of arrow 196. A suitable chemical array autofocus system is described in pending U.S. patent application Ser. No. 09/415,184 for "Apparatus And Method For Autofocus" by Dorsel et al., filed Oct. 7, 1999, incorporated herein by reference, as well as European publication EP 1091229 published Apr. 11, 2001 under the same title and inventors.

Controller 180 of the apparatus is connected to receive signals from detectors 150a, 150b (these different signals being different "channels"), namely a signal which results at each of the multiple detected wavelengths from emitted light for each scanned pixel on array 12 when at the reading position mounted in holder 200. Controller 180 also receives the signal from autofocus offset detector 170, and provides the control signal to EOM 110, and controls the scan system. Controller 180 may also analyze, store, and/or output data relating to emitted signals received from detectors 150a, 150b in a known manner. Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 40). Controller 180 is suitably programmed to execute all of the steps required by it during operation of the apparatus, as discussed further below. Alternatively, controller 180 may be any hardware or hardware/software combination which can execute those steps.

In one mode of operation, the array in package 30 is typically first exposed to a liquid aqueous sample (for example, placed directly on substrate 10). The array may then be washed with buffer then water, and dried following washing then inserted into a scanner for reading. Drying may be accomplished using any suitable drying method and conditions which will not decompose the probes and their bound targets, such as any suitable one or more of: air drying at room temperature or raised temperature; reduced pressure; centrifuging; or exposure to a dry unreactive gas stream (such as dry nitrogen). Following a given array package 30 being mounted in the apparatus, the identifier reader may automatically (or upon operator command) read array ID 40, and use this to retrieve information on the array layout as well as an instruction that the array should be interrogated and read from a forward position. Such information may be retrieved directly from the contents of identifier 40 when ID 40 contains such information. Alternatively, identifier 40 may be used to retrieve such information from a database containing the identifier in association with such information. Such a database may be a local database accessible by controller 180 (such as may be contained in a portable storage medium in drive 182 which is associated with package 30, such as by physical association with package 30 when received by the user, or by a suitable identification), or may be a remote database accessible by controller 180 through communication module 184 and a suitable communication channel (not shown). The retrieved instruction on how the array should be interrogated and read, can be used by controller 180 to check that the array is oriented within an array reader such that the array can be interrogated and read by the reader from the forward position. Controller 180 may do this based on the orientation of identifier 40 in holder 200. This may be done by checking whether the identifier 40 is facing focuser 160 or not. To determine this, two identifier readers may be provided facing respective surfaces 11a, 11b of a mounted substrate 10, such that each will only be able to read identifiers (or some other indicia on one side 11a or 11b only) on the side 11a or 11b which it faces. Controller 180, knowing that the read identifier is on a particular side of substrate 10 (which information can also be retrieved in the manner earlier described, based on the identifier), and which identifier reader successfully read the identifier, can determine the orientation of the mounded substrate 10 in the array reader.

The saved results from a sample exposed array, read according to a method of the present invention, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing).

It will be appreciated that various modifications can be made to the present invention. For example, while an interrogating light is directed from a position forward of the front surface of the array, this does not mean that the original light source (such as a laser) needs to be positioned in front of the front surface as long as the light is directed onto the front surface 11a without going through the substrate. Similarly, the detectors need not be positioned in front of the front surface as long as the emitted light which is detected has not traveled through the substrate (for example, the detectors could be behind the front surface with a suitable mirror combination to collect emitted light traveling away from the front surface 11a in the forward direction). It will also be appreciated that more than one anti-reflection layer may be used, with each having a thickness that is approximately equal to $0.25\lambda$ in a known manner for anti-reflection coatings in other optics applications. While the emitted light has been referenced as fluorescence in the examples above, it will be appreciated that the light emitted from the locations (such as the labels) can be the result of any other process (for example, chemi-luminescence).

Note also that a variety of geometries of the features 16 may be constructed other than the organized rows and columns of the array of FIGS. 2–4. For example, features 16 can be arranged in a series of curvilinear rows across the substrate surface (for example, a series of concentric circles or semi-circles of spots), and the like. Even irregular arrangements of features 16 can be used, at least when some means is provided such that during their use the locations of features of particular characteristics can be determined (for example, a map of the features is provided to the end user with the array). Furthermore, substrate 10 could carry more than one array 12, arranged in any desired configuration on substrate 10. While substrate 10 is planar and rectangular in form, other shapes (for example, circular) could be used with housing 34 being adjusted accordingly. In many embodiments, substrate 10 will be shaped generally as a planar, rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used. Less preferably, substrate 10 could have three-dimensional shape with irregularities in first surface 11a. In any event, the dimensions of housing 34 may be adjusted accordingly. Additionally, during scanning it is possible to illuminate all pixels of a line simultaneously (for example, by using a line of light emitting diodes).

Other various modifications to the particular embodiments described above are, of course, possible. Accordingly, the present invention is not limited to the particular embodiments described in detail above.

What is claimed is:

1. A method of interrogating an addressable array unit having a substantially unreflective substrate with a front surface, and a dry array on the front surface having a plurality of different chemical features, the method comprising:
   (a) directing an interrogating light from a position forward of the front surface onto the chemical features of the dry array; and
   (b) detecting light directed in a forward direction from respective features in response to the interrogating light;
   wherein the detected emitted light is from locations of the features positioned within a ⅛ wavelength of an antinode resulting from either directly incident interrogating light and interrogating light reflected by the substrate, or from directly detected emitted light and emitted light reflected by the substrate.

2. A method according to claim 1 wherein the chemical features comprise polynucleotides of different sequence.

3. A method according to claim 1 wherein the detected light is emitted from locations which are spaced from the front surface by a distance d wherein:

$$n\lambda/8 < d < (n+2)\lambda/8$$

in which n is n=1, 5, 9, 13, or 17, and $\lambda$ is the wavelength of the interrogating light or emitted light.

4. A method according to claim 3 wherein the detected light is emitted from locations which are spaced from the front surface by a distance d wherein:

$$0.15\lambda < d < 0.35\lambda.$$

5. A method according to claim 4 wherein:

$$0.20\lambda < d < 0.30\lambda.$$

6. A method according to claim 1 wherein the detected light power density for a feature is within 25% of a maximum attainable under the same conditions with only the distance of the emitting locations from the front surface being varied.

7. A method according to claim 1 wherein the interrogating light is directed toward the front surface at an angle of between 0 and 36 degrees to a normal to the front surface.

8. A method according to claim 1 wherein the substrate has a refractive index of at least 1.3.

9. A method according to claim 1 wherein the substrate is a plastic, glass or silica.

10. A method comprising receiving data representing a result of an interrogation obtained by the method of claim 9.

11. A method of interrogating an addressable array unit having a substantially unreflective substrate with a front surface, and a dry array on the front surface having a plurality of different chemical features, the method comprising:
   (a) directing interrogating light from a position forward of the front surface onto the chemical features of the dry array; and
   (b) detecting light directed in a forward direction which is emitted from respective features in response to the interrogating light;
   wherein the detected light power density for each of multiple features is within 30% of a maximum attainable under the same conditions with only the distance of the emitting locations from the front surface being varied.

12. A method according to claim 11 wherein the detected light power density for each of multiple features is within 20% of the maximum attainable.

13. A method of interrogating an addressable array unit having a transparent substrate with a front surface, and a dry array on the front surface having a plurality of different chemical features, the method comprising:
   (a) directing interrogating light from a position forward of the front surface onto the chemical features of the dry array; and
   (b) detecting light directed in a forward direction which is emitted from respective features in response to the interrogating light;
   wherein the substrate includes a transparent layer extending between the front surface of the substrate to a next layer of the substrate, and which transparent layer has a of thickness t where:

$$n\lambda 8 < t < (n+2)\lambda 8$$

in which n=1, 5, 9, 13, or 17, and $\lambda$ is the wavelength of the interrogating or emitted light.

14. A method according to claim 13 wherein:

$$0.15n\lambda < t < 0.3n\lambda.$$

15. A method according to claim 14 wherein:

$$0.20\lambda < t < 0.30\lambda.$$

16. A method according to claim 13 wherein n3/n2 minus n2/n1 is less than 0.3, in which n3, n2, and n1 are the refractive indices of the next layer, transparent layer, and the medium adjacent the front surface, respectively.

17. A method according to claim 16 wherein the transparent layer has an index of refraction of less than 1.3.

18. A method according to claim 17 wherein the transparent layer has an index of refraction of less than 1.2.

19. A method according to claim 13 wherein the transparent layer is an anti-reflective layer which reduces the light power density of reflected light to at least 50% of that which would be reflected from the substrate under the same conditions but with the anti-reflective layer absent.

20. A method according to claim 19 wherein the detected light power density for a feature is at least 25% greater than attained under the same conditions but with the anti-reflection layer absent.

21. A method according to claim 19 wherein the detected light power density for a feature is at least 33% greater than attained under the same conditions with the anti-reflection layer absent.

22. A method according to claim 19 wherein the detected light power density for a feature is at least 50% greater than attained under the same conditions with the anti-reflection layer absent.

23. A method according to claim 13 wherein the interrogating light is directed toward the front surface at an angle of between 0 and 36 degrees to a normal to the front surface.

24. A method according to claim 13 wherein the refractive index of the next layer of the substrate is at least 1.3.

25. A method according to claim 19 wherein the refractive index of the anti-reflective layer is at least 1.2.

26. A method according to claim 24 wherein the refractive index of the next layer of the substrate is at least 1.4.

27. A method according to claim 24 wherein the next layer is selected from a plastic, glass, or silica.

28. A method according to claim 27 wherein the next layer has a thickness of at least 1 micrometer.

29. A method according to claim 13 wherein the interrogating light is laser light.

30. A method according to claim 13 wherein at least some of the features include a fluorescent label and the detected emitted light is fluorescence from the label.

31. A method according to claim 30 wherein the features include corresponding moieties linked to the substrate, the method additionally comprising, prior to illuminating the features, exposing the features to a sample such that at least some of the features bind to respective moieties in the sample which sample moieties include the fluorescent label.

32. A method comprising forwarding data representing a result of an interrogation obtained by the method of claim 13.

33. A method according to claim 32 wherein the data is communicated to a remote location.

* * * * *